United States Patent [19]

Thame

[11] Patent Number: 4,853,213

[45] Date of Patent: Aug. 1, 1989

[54] USE OF PERIWINKLE IN ORAL HYGIENE

[75] Inventor: Neville Thame, Montclair, N.J.

[73] Assignee: Peri-Oral Dental Products, Inc., Teaneck, N.J.

[21] Appl. No.: 168,989

[22] Filed: Mar. 16, 1988

Related U.S. Application Data

[63] Continuation of Ser. No. 840,019, Mar. 17, 1986, abandoned.

[51] Int. Cl.$^4$ .......................... A61K 7/26; A61K 7/16; A61K 7/18
[52] U.S. Cl. ........................................ 424/58; 424/49; 424/52; 424/55; 424/56; 424/57; 514/900; 514/901; 514/902
[58] Field of Search ...................... 424/49, 52, 55–58; 514/900–902

[56] References Cited

U.S. PATENT DOCUMENTS

| | | | |
|---|---|---|---|
| 3,119,743 | 1/1964 | Ericsson | 424/52 |
| 3,888,976 | 6/1975 | Mikvy | 424/44 |
| 4,328,231 | 3/1982 | Zajer nee Balazs et al. | |

FOREIGN PATENT DOCUMENTS 0016814 1/1984 Japan.
0163810 8/1985 Japan.

OTHER PUBLICATIONS

*Chem. Abst.*, 104, 304 (1986) Abst. No. 10428a.
*Chem. Abst.*, 103, 301 (1985), Abst. No. 11246f.
*Chem. Abst.*, 99, 327 (1983), Abst. No. 200365d.
*Chem. Abst.*, 84, 350 (1976), Abst. No. 140622p.
Grieve, *A Modern Herbal*, vol. II, Dover Publication 1982, pp. 629–631.
John Lust, *The Herb Book*, Bantam Books, p. 333.
Robertson, Diane; *Jamaican Herbs*, 1982, 1 page.
Eli Lilly Co.; "VELBAN" fact sheet; (2 pp.).
Eli Lilly Co.; "ONCOVIN" fact sheet; (2 pp).
Tokumaru and Avitabile, "Suppression of Herpes Simplex Virus Infection by Antimitotic Substances in the Rabbit Cornea"; *Proc. Soc. Exp. Biol. Med.;* 1971; pp. 29–34.
Boulware, R. T. and Southard, G. L., "Sanguinarine in the Control of Volatile Sulfur Compounds in the Mouth: A Comparative Study"; Compendium of Continuing Education in Dentistry; 1984; Supplement No. 5; pp. S61–A64.
Yankell, S. L.; "Saliva Glycolysis and Plaque"; *Compendium of Continuing Education in Dentistry;* 1984; Supplement No. 5; pp. S57–S60.
Hutchinson, J.; *The Families of Flowering Plants;* 1959; vol. I, 2nd Ed.; pp. 75–83, 96–99, 178–179, 380–381.
Jaques, H. E.; *Plant Families How to Know Them;* 1949; 2nd Ed.; pp. 138–139, 144–145, 154–163.
Gleason, Henry A., Ph.D. and Cronquist, Arthur, Ph.D.; *Manual of Vascular Plants of Northeastern United States and Adjacent Canada;* 1963; pp. 554–555, 654–657.
G. Garnier et al.: "Ressources Medicinales de la Flore Francaise" Tome II, 1961, Vigot Freres Editeurs, (Paris, FR) pp. 1007–1011.

*Primary Examiner*—Howard E. Schain
*Assistant Examiner*—F. T. Moezie
*Attorney, Agent, or Firm*—Samuelson & Jacob

[57] ABSTRACT

Oral hygiene methods for reducing plaque and for the treatment of periodontal diseases of bacterial etiology by significantly reducing bacterial activity in the oral cavity through the inclusion of about 0.03% to at least about 10% by weight of a dried methanol extract of the perennial herb periwinkle in compositions and applying the compositions to the oral cavity.

13 Claims, No Drawings

USE OF PERIWINKLE IN ORAL HYGIENE

This application is a continuation of application Ser. No. 840,019, filed Mar. 17,1986 now abandoned.

FIELD OF THE INVENTION

The invention relates to oral hygiene compositions and their use.

BACKGROUND OF THE INVENTION

Chemicals extracted from the periwinkle plant (*Vinca major, Vinca minor* and *Vinca rosea*) have found extensive use in the treatment of many ailments. It has been shown that two of the active compounds in this plant are dimeric alkaloids known as vincristine and vinblastine, sold under the names of "Oncovin®" and "Velban®", respectively. Numerous studies have demonstrated the use of these two extracts in the treatment of various forms of cancer. For example, vincristine has been used in the treatment of acute leukemia and may be used in combination with other oncolytic agents for the treatment of Hodgkin's disease, lymphosarcoma, reticulum-cell sarcoma, rhabdomyosarcoma, neuroblastoma and Wilm's tumor. Vinblastine is indicated in the treatment of Hodgkin's disease, Kaposi's sarcoma, mycosis fungoides, various types of lymphomas, and other carcinomas.

Vincristine and vinblastine have been shown to be capable of suppressing herpes simplex virus infections. (Tokumaru and Avitabile, *Proc. Soc. Exp. Biol. Med.*, 1971). U.S. Pat. No. 4,328,231 discloses a class of compounds, at least some of which can be isolated from *Vinca minor*, useful in treating skin diseases such as psoriasis.

Folklore has attributed curative properties to the periwinkle plant. It has been recommended as a remedy for diarrhea and hemorrhages. A tea made from the plant can be used for nervous conditions. It was thought to be a cure for diabetes. Chewing the herb has been recommended to stop toothache or to stop bleeding in the mouth and nose. Another source also reports its use as a laxative, for cramp, and for skin inflammation, and suggests the use of *Vinca major* as a gargle in cases of scurvy, sore throat and inflamed tonsils.

The present invention uses periwinkle extract for several oral hygiene purposes. These include plaque reduction, control of volatile sulfur compounds (which is related to breath freshening), cleaning of the teeth and conditioning of gum tissue, and relieving the symptoms of gingivitis. The extract appears to possess antimicrobial properties.

SUMMARY OF THE INVENTION

The present invention relates to compositions which are useful and convenient for improving various aspects of oral hygiene. These compositions, which may be used in tooth cleansing and mouthwash formulations, comprise an extract from the perennial herb periwinkle (*Vinca major, Vinca minor* or *Vinca rosea*), also known as myrtle and ramgoat roses.

The tooth cleansing composition may be in the form of toothpaste, tooth powder or mouthwash, or any form suitable for use in the oral cavity, including a salve, breath spray or chewing gum, but for ease of application, the toothpaste and mouthwash are preferred. The compounds of the invention may also be coated on oral hygiene accessories, such as dental floss.

The extract of periwinkle is compatible with other agents commonly found in toothpaste, and when formulated with them, it does not possess the bitter, sharp and burning taste of the plant.

In order to obtain the beneficial effects of the periwinkle extract, its concentration may vary preferably from about 0.03% to about 10%, in the toothpaste and mouthwash formulations.

DETAILED DESCRIPTION

The extract of periwinkle is preferably produced by slurrying the finely divided dried plant and treating it with methanol at elevated temperatures. For example, the finely divided dried plant is mixed with methanol and stirred at 60° C. for approximately 3 hours. The methanol is separated through filtration and then evaporated to dryness. The residue is dissolved in chloroform and made acidic by the addition of concentrated hydrochloric acid. In some instances it is preferable to use the periwinkle extract without acidification; such as in the case when it is formulated with sodium bicarbonate. The mixture is filtered and subsequently the filtrate is evaporated to dryness. The resultant solid, is then taken up in a carrier such as glycerin, as described in the formulas for Additives A and B, below.

Additives are made by combining the periwinkle extract with other ingredients such as glycerin and water. Examples of these Additives are as follows:

| Additive A | |
|---|---|
| Component | % by Wt. |
| Glycerin | 87.8 |
| Water (distilled) | 11.0 |
| Sodium Bicarbonate | 0.65 |
| Periwinkle Extract | 0.55 |

| Additive B | |
|---|---|
| Component | % by Wt. |
| Glycerin | 75.8 |
| Water (distilled) | 10.1 |
| $ZnCl_2$ | 13.6 |
| Periwinkle Extract | 0.5 |

To prepare Additive A, the sodium bicarbonate is dissolved in the distilled water and this solution is added to the glycerin with stirring until a homogeneous solution is made. To this mixture is added the periwinkle extract and the mixture is stirred until all the periwinkle extract is incorporated.

To prepare Additive B, $ZnCl_2$ is dissolved in distilled water and the resulting solution is added to the glycerin with stirring and heated to 60° C. until a homogeneous solution is obtained. The periwinkle extract is stirred into the mixture until it is incorporated. The resulting Additive mixtures may then be used to formulate a toothpaste, mouthwash or other product. In the formulas given below, the percent by weight of periwinkle extract in the final product is listed. When preparing these formulations, however, it is more convenient, and therefore preferable, to add the ingredient in the form of one of the Additives.

EXAMPLE 1

Preparation of a toothpaste containing periwinkle extract and sodium bicarbonate.

| Materials | % by Wt. |
|---|---|
| Sodium Bicarbonate | 50 |
| Glycerin | 31.2 |
| CARBOWAX 3350 TM | 5 |
| CARBOWAX 400 TM | 10 |
| Sodium Saccharin | 1.5 |
| Sodium Fluoride | 0.1 |
| Sodium Lauryl Sulfate | 0.8 |
| Flavoring | 1.0 |
| Periwinkle Extract | .4 |

The periwinkle Additive A as prepared above is added to glycerin, then the sodium bicarbonate is added and the mixture is stirred until a smooth paste is obtained. The CARBOWAX 3350 TM and CARBOWAX 400 TM are added and the mixture is stirred until all ingredients are completely incorporated. The flavoring, sweetener (sodium saccharin), sodium lauryl sulfate, and sodium fluoride are then added with stirring until a homogeneous mixture is obtained.

EXAMPLE 2

Preparation of a toothpaste containing periwinkle extract, sodium bicarbonate and aloe vera extract.

| Materials | % by Wt. |
|---|---|
| Sodium Bicarbonate | 35.0 |
| Glycerin | 22.8 |
| Water (distilled) | 10.0 |
| Calcium Carbonate | 10.0 |
| Aloe Vera Extract | 15.0 |
| Cellulose Gum | 2.0 |
| Sodium Lauryl Sulfate | 0.8 |
| Flavoring | 1.2 |
| Titanium Dioxide | 1.0 |
| Periwinkle Extract | 0.3 |
| Chlorophyllin Copper Complex | 0.7 |
| Tetrasodium Pyrophosphate | 1.2 |

To a mixture of glycerin and water are added sodium bicarbonate and calcium carbonate. This mixture is stirred until a smooth paste is obtained. Aloe vera extract and periwinkle Additive A are added with stirring until a homogenous mixture is obtained. Cellulose gum, sodium lauryl sulfate, flavoring, titanium dioxide, Chlorophyllin copper complex and tetrasodium pyrophosphate are then added and the mixture is stirred until the desired consistency is obtained.

EXAMPLE 3

Preparation of a toothpaste containing periwinkle extract and zinc chloride.

| Materials | % by Wt. |
|---|---|
| Glycerin | 19.0 |
| POLYSORBATE 80 TM | 2.0 |
| Calcium pyrophosphate | 5.0 |
| Sodium Lauryl Sulfate | 0.8 |
| Zinc Chloride | 0.1 |
| Flavoring | 0.6 |
| Dicalcium phosphate | 27.0 |
| Calcium Carbonate | 24.2 |
| Periwinkle Extract | 0.3 |
| Water (distilled) | 21.0 |

To a mixture of glycerin and half the amount of distilled water are added the calcium pyrophosphate, dicalcium phosphate and calcium carbonate with stirring until a smooth paste is obtained. To this paste is added zinc chloride and periwinkle Additive B; these are incorporated into the paste until a homogeneous mixture is obtained. Finally the flavoring, sodium lauryl sulfate, POLYSORBATE 80 TM and the remaining water are incorporated with stirring to produce the desired consistency of toothpaste.

The above toothpastes when used in the normal manner one or more times per day are excellent cleansing agents and breath fresheners. When used over an extended period, the bleeding associated with vigorous brushing tends to be reduced, and the condition of the tissue appears to be benefitted.

EXAMPLE 4

PREPARATION OF AN ORAL RINSE CONTAINING PERIWINKLE EXTRACT

The extract of the periwinkle herb was combined with other ingredients usually found in oral rinse compositions to make a product that exhibits properties superior to commercially available products.

| Materials | % by Wt. |
|---|---|
| Ethyl Alcohol | 10.0 |
| Periwinkle Extract | 0.03 |
| Citric Acid | 0.03 |
| Flavoring oil of winter green | 0.25 |
| Glycerin | 3.79 |
| Water (distilled) | 85.00 |
| Sodium Lauryl Sulfate | 0.10 |
| POLYSORBATE 80 TM | 0.60 |
| Zinc Chloride | 0.20 |

In the formulation of the oral rinse and the toothpastes, it is preferable to include sudsing agents, such as sodium lauryl sulfate, to aid in the penetration of the film which forms on teeth. The sudsing agent carries the active ingredients into crevices in the mouth to sites where the active ingredients can attack plague and bacteria. Suitable sudsing agents are those which are reasonably stable throughout a wide pH range. They may be nonsoap, nonionic, cationic or amphoteric organic synthetic detergents.

Test Results Demonstrating Plaque Reduction and Control of Volatile Sulfur Compounds The oral rinse prepared according to Example 4 with the Additive containing an extract of periwinkle and $ZnCl_2$ and containing an appropriate sudsing agent exhibits properties beneficial to the teeth and other tissues of the oral cavity. For example, it is well known that without the removal or the deactivation of the sticky mass (plaque) that adheres to the teeth, the gums become sore and bleed easily when brushed. Therefore any agent that helps to reduce the level of this sticky mass is beneficial to the teeth and gums.

A comparison of test results of an oral rinse of this invention with a commercially available plaque reducing and malodor reduction rinse illustrates the effectiveness of the present invention against plaque and odor-forming bacteria.

Plaque Reduction

Plaque formation during a three day experimental period was compared in 2 males and 1 female volunteer using two compositions of the present invention and a placebo. The formula for the periwinkle & $ZnCl_2$ oral rinse is that given in Example 4. The other periwinkle rinse is of the same formulation, with periwinkle extract forming 0.03% by weight of the product, except that the $ZnCl_2$ is omitted. (the $ZnCl_2$ is also omitted from the Additive B preparation).

The teeth of all subjects were cleaned free of plaque and calculus corroborated by disclosure with the standard basic fuschin. This was followed by a three-day period of brushing with a commercial non-fluoride dentifrice and no use of the test mouthrinse. At the end of this period the plaque scores were determined using the method of Quigley and Hein. A score of 0 to 5 was assigned to each facial and lingual nonrestored surface using teeth 3, 9, 12, 25 and 29. In this manner a baseline was determined. After the baseline period each subject was assigned another blank control period and then two periods each on test and control mouthwashes.

During each 3 day trial period, with the exception of the two blank control periods, the subjects were instructed to use 20 ml of mouthwash as a rinse 2 times daily. At the end of the trial period plaque scores were again determined.

Results of this study are shown in Table 1.

TABLE 1

Plaque Indices and Percent Plaque Reduction of Periwinkle Oral Rinses
Scale = 0 to 5.0

| Group | Baseline (Day 0) | Post Treatment (Day 3) | Percent Reduction |
|---|---|---|---|
| Placebo | 2.58 | 2.88 | +11.63 |
| Periwinkle & $ZnCl_2$ | 2.64 | 2.15 | −18.56 |
| Periwinkle | 2.55 | 2.20 | −14.28 |

The effectiveness of the periwinkle oral rinse in controlling plaque growth was demonstrated as summarized in Table 1. The plaque score when the placebo was used did not drop but increased from 2.58 for a 11.63% plaque growth. The plaque scores with the zinc containing compound were reduced from 2.64 to 2.15, corresponding to a reduction of 18.56%. The difference between the two groups corresponds to a 20.19% difference between placebo and periwinkle rinse containing zinc. Users of the periwinkle rinse without $ZnCl_2$ also exhibited a significant lowering of the plaque scores, from 2.55 to 2.20, a 14.28% decrease which corresponds to a difference of 25.91% between the placebo and this rinse.

Control of Volatile Sulfur Compounds

It has been reported that volatile sulfur compounds (VSC) are produced in the oral cavity. It has been stated that the tongue acts as a major reservoir of VSC and that these VSC originate mainly in salivary sediment, a mixture of cellular debris and microorganisms that use sediment constituents as proteinaceous substrates. The VSC so formed can be detected by using lead acetate-impregnated strips above the headspace of putrifying saliva, as well as by breath malodor. (Boulware and Southard, Compendium of Continuing Education in Dentistry, Supplement No. 5, 1984.)

Aside from the obvious cosmetic implication of breath malodor, the presence of these reactive sulfides in the mouth can have significant physiologic consequences. For example, hydrogen sulfide, a well-known irritant which is produced in the oral cavity, has been implicated in the solubilization of gingival collagen and may even alter the permeability of the cervicular epithelium. Similarly, evidence suggests that methyl mercaptan inhibits the synthesis of protein and collagen at concentrations of 10 ng/ml. Control of these VSC found in the oral cavity would be desirable both for health and cosmetic reasons.

Two male subjects were asked to rinse with an oral rinse of the formula given in Example 4, "Listerine ®" mouthrinse (which is a mixture of essential oils) or water. Immediately before product use and before normal morning oral hygiene approximately 2 ml of saliva was collected in a 15×150 mm glass test tube and the tube was immersed in an ice bath. This procedure was repeated 45 minutes after product use. Crossover studies were conducted in which the procedure was repeated using "Listerine ®" as the test wash. The saliva samples were incubated at 25° for 24 hours with a lead acetate-impregnated test strip suspended in the head space. The lead acetate papers were read on an empirical scale of 0 to 3 as a function of discoloration. (This was the method of testing and scoring used by Boulware and Southard.) The results are shown in Table 2.

TABLE 2

VSC Levels in Headspace Above Incubated Saliva As Scored by Lead Acetate Papers:
Saliva Collected 45 mins. After Oral Rinse
Scale = 0 to 3.0

| Oral Rinse | VSC Score |
|---|---|
| Periwinkle & $ZnCl_2$ | .1 |
| "LISTERINE ®" | 2.4 |
| Water | 3.0 |

Clearly, the product containing the periwinkle extract was superior to the commercially available product. It was approximately 24 times more effective than "Listerine ®" when compared by this method.

Saliva Glycolysis Assay

The saliva glycolysis assay has been used to predict the clinical effectiveness of antiplaque agents. (Yankell, Compendium of Continuing Education in Dentistry, Supplement No. 5,1984.) Such studies are based on the fact that during glycolysis the bacterial of the oral cavity produce acidic by-products which lower the pH of whole saliva.

The study was performed to compare a placebo (water), "Listerine ®" and the oral rinse described in Example 4. Three subjects, 2 male and 1 female, were instructed to rinse with a test rinse. Four ml of saliva was collected from each person at 15 and 45 minutes after rinsing. Each saliva sample with the addition of 5% sucrose was incubated at 25° C. for 5 hours and the pH of the mixture recorded at 1 hour intervals. The study was done in a crossover design such that each person used each of the test solutions on different days. The results of these experiments are shown in Table 3 and Table 4.

TABLE 3

| | pH of Sample Collected 15 Minutes After Use of Rinse | | | | | |
|---|---|---|---|---|---|---|
| Time-Hrs. | 0 | 1 | 2 | 3 | 4 | 5 |
| Water | 6.3 | 5.6 | 5.3 | 5.0 | 4.9 | 4.7 |
| "LISTERINE ®" | 6.8 | 6.5 | 6.3 | 6.1 | 5.9 | 5.5 |
| Periwinkle | | | | | | |

TABLE 3-continued

| | pH of Sample Collected 15 Minutes After Use of Rinse | | | | | |
|---|---|---|---|---|---|---|
| Time-Hrs. | 0 | 1 | 2 | 3 | 4 | 5 |
| & ZnCl$_2$ | 6.5 | 6.5 | 6.6 | 6.6 | 6.5 | 6.5 |

TABLE 4

| | pH of Sample Collected 45 Minutes After Use of Rinse | | | | | |
|---|---|---|---|---|---|---|
| Time-Hrs. | 0 | 1 | 2 | 3 | 4 | 5 |
| Water | 6.2 | 6.2 | 5.7 | 5.4 | 5.0 | 4.9 |
| "LISTERINE ®" | 6.8 | 6.6 | 6.4 | 6.0 | 5.8 | 5.6 |
| Periwinkle & ZnCl$_2$ | 6.6 | 6.6 | 6.5 | 6.5 | 6.4 | 6.5 |

The periwinkle extract rinse was better able to retard the decrease in pH than were either "Listerine ®" or water. These results indicate that there is not only significant reduction in bacterial activity by using the periwinkle extract in an oral rinse but also that the beneficial effects of the extract continue in the saliva for some time after use. This ability of the periwinkle extract to be retained in the saliva is important because it provides protection for significant periods of time after use. The pH of samples collected 15 and 45 minutes after use of the periwinkle extract oral rinse was measured again 10 hours after use as 5.8 and 6.0, respectively. These results further demonstrate the long-lasting effect of the periwinkle extract oral rinse.

The present invention can be used in several forms, and has numerous beneficial effects on oral hygiene. The invention should not be considered to be limited to te specific formulas given herein, but rather as encompassing equivalent preparations.

The embodiments of the invention in which an exclusive property or privilege is claimed are defined as follows:

1. An oral hygiene method for reducing plaque and for the treatment of periodontal diseases of bacterial etiology, the method comprising reducing bacterial activity in the oral cavity by applying to the oral cavity a composition containing from about 0.3% to about 50% by weight of a dried methanol extract from the perennial herb periwinkle.

2. The method of claim 1 wherein the composition is in the form of an oral rinse composition.

3. The method of claim 2 wherein the composition includes a surface active agent.

4. The method of claim 2 wherein the composition includes ethyl alcohol, citric acid, flavoring oil of wintergreen, distilled water, sodium lauryl sulfate, polyoxyethylene 80 sorbitan monolaurate and zinc chloride.

5. The method of claim 1 wherein the composition is in the form of a toothpaste composition.

6. The method of claim 5 wherein the composition includes a surface active agent.

7. The method of claim 5 wherein the composition includes a surface active agent and glycerin.

8. The method of claim 5 wherein the composition includes sodium bicarbonate, glycerin, polyethylene glycol powder, polyethylene glycol liquid, sodium saccharin, sodium fluoride, sodium lauryl sulfate and flavoring.

9. The method of claim 5 wherein the composition includes sodium bicarbonate, glycerin, distilled water, calcium carbonate, aloe vera extract, cellulose gum, sodium lauryl sulfate, flavoring, titanium dioxide, chlorophyllin copper complex and tetrasodium pyrophosphate.

10. The method of claim 5 wherein the composition includes glycerin, polyoxyethylene 80 sorbitan monolaurate, calcium pyrophosphate, sodium lauryl sulfate, zinc chloride, flavoring, dicalcium phosphate, calcium carbonate and distilled water.

11. An oral hygiene method for reducing plaque and for the treatment of periodontal diseases of bacterial etiology, the method comprising reducing bacterial activity in the oral cavity by applying to the oral cavity a composition containing from about 0.03% to about 10% by weight of a dried methanol extract from the perennial herb periwinkle.

12. The method of claim 11 wherein the composition is in the form of an oral rinse composition.

13. The method of claim 11 wherein the composition is in the form of a toothpaste composition.

* * * * *